(12) United States Patent
Efremkin (10) Patent No.: US 11,737,780 B2
(45) Date of Patent: Aug. 29, 2023

(54) DEVICES AND METHODS FOR INTRABODY SURGERY

(71) Applicant: Pavel V. Efremkin, Tarrytown, NY (US)

(72) Inventor: Pavel V. Efremkin, Tarrytown, NY (US)

(*) Notice: Subject to any disclaimer, the term of this patent is extended or adjusted under 35 U.S.C. 154(b) by 106 days.

(21) Appl. No.: 17/475,516

(22) Filed: Sep. 15, 2021

(65) Prior Publication Data
US 2022/0054162 A1 Feb. 24, 2022

Related U.S. Application Data (62) Division of application No. 16/192,781, filed on Nov. 15, 2018, now abandoned.
(Continued)

(51) Int. Cl.
*A61B 17/32* (2006.01)
*A61B 17/3207* (2006.01)
(Continued)

(52) U.S. Cl.
CPC .. *A61B 17/320758* (2013.01); *A61B 17/2202* (2013.01); *A61B 17/320068* (2013.01);
(Continued)

(58) Field of Classification Search
CPC ........ A61B 17/320758; A61B 17/2202; A61B 17/320068; A61B 18/1492; A61B 18/245; A61B 18/1206; A61B 18/26; A61B 2017/00022; A61B 2017/003; A61B 2017/00323; A61B 2017/00544; A61B 2017/00685; A61B 2017/22024; A61B 2017/22042; A61B 2017/22094; A61B 2017/306; A61B 2017/320069; A61B 2017/32007; A61B 2017/320716; A61B 2017/320775; A61B 2018/00422; A61B 2018/00505; A61B 2018/00511; A61B 2018/00577; A61B 2018/00601; A61B 2018/00642; A61B 2018/0066; A61B 2018/00702; A61B 2018/00791; A61B 2018/00875; A61B 2018/00904; A61B 2090/08021; A61B 2217/005; A61B 2217/007; A61B 2218/007; A61N 7/00;
(Continued)

(56) References Cited

U.S. PATENT DOCUMENTS

2002/0007190 A1* 1/2002 Wulfman ....... A61B 17/320758
606/171
2008/0004644 A1* 1/2008 To .................. A61B 17/320783
606/159

* cited by examiner

*Primary Examiner* — Amanda K Hulbert
*Assistant Examiner* — Natasha Patel
(74) *Attorney, Agent, or Firm* — Lawrence G. Fridman, ESQ; Feigin & Fridman, LLC (57) ABSTRACT

A method for conducting intrabody surgery by means of a surgical device having a cutting arrangement actuated by a driveshaft and rotationally supported by the guide wire. A receiving cannel extends through the cutting arrangement and movably receives the guidewire. A plurality of sensors is provided within the cutting arrangement to emit signals capable of changing parameters depending on the composition of the occlusion, so as to allow the control unit to generate signals controlling operation of the cutting arrangement. The method includes the steps of detecting parameters within the intrabody area by the sensors to controlling operation of the cutting arrangement with the power and control unit.

14 Claims, 8 Drawing Sheets

Related U.S. Application Data (60) Provisional application No. 62/680,260, filed on Jun. 4, 2018, provisional application No. 62/586,654, filed on Nov. 15, 2017.

(51) Int. Cl.
| | |
|---|---|
| *A61B 18/14* | (2006.01) |
| *A61B 18/24* | (2006.01) |
| *A61B 17/22* | (2006.01) |
| *A61N 7/00* | (2006.01) |
| *A61B 18/00* | (2006.01) |
| *A61B 17/00* | (2006.01) |
| *A61B 18/12* | (2006.01) |
| *A61N 7/02* | (2006.01) |
| *A61B 18/26* | (2006.01) |
| *A61B 90/00* | (2016.01) |
| *A61B 17/30* | (2006.01) |

(52) U.S. Cl.
CPC ........ *A61B 18/1492* (2013.01); *A61B 18/245* (2013.01); *A61N 7/00* (2013.01); *A61B 18/1206* (2013.01); *A61B 18/26* (2013.01); *A61B 2017/003* (2013.01); *A61B 2017/00022* (2013.01); *A61B 2017/00323* (2013.01); *A61B 2017/00544* (2013.01); *A61B 2017/00685* (2013.01); *A61B 2017/22024* (2013.01); *A61B 2017/22042* (2013.01); *A61B 2017/22094* (2013.01); *A61B 2017/306* (2013.01); *A61B 2017/32007* (2017.08); *A61B 2017/320069* (2017.08); *A61B 2017/320716* (2013.01); *A61B 2017/320775* (2013.01); *A61B 2018/0066* (2013.01); *A61B 2018/00422* (2013.01); *A61B 2018/00505* (2013.01); *A61B 2018/00511* (2013.01); *A61B 2018/00577* (2013.01); *A61B 2018/00601* (2013.01); *A61B 2018/00642* (2013.01); *A61B 2018/00702* (2013.01); *A61B 2018/00791* (2013.01); *A61B 2018/00875* (2013.01); *A61B 2018/00904* (2013.01); *A61B 2090/08021* (2016.02); *A61B 2217/005* (2013.01); *A61B 2217/007* (2013.01); *A61B 2218/007* (2013.01); *A61N 7/02* (2013.01); *A61N 2007/0039* (2013.01); *A61N 2007/0043* (2013.01); *A61N 2007/0065* (2013.01)

(58) Field of Classification Search
CPC .............. A61N 7/02; A61N 2007/0039; A61N 2007/0043; A61N 2007/0065
See application file for complete search history.

DEVICES AND METHODS FOR INTRABODY SURGERY

CROSS-REFERENCE TO RELATED APPLICATION

The present application is Divisional Application of currently pending patent application Ser. No. 16/192,781 filed Nov. 15, 2018 which claims priority of Provisional Patent Application Ser. No. 62/586,654 filed by the Applicant on Nov. 15, 2017 and Provisional Patent Application Ser. No. 62/680,260 filed by the Applicant on Jun. 4, 2018, the entire disclosure of these applications is hereby incorporated by reference.

FIELD OF THE INVENTION

The devices and methods of the invention generally relate to intrabody surgery and to treatment of occluded body lumens. In particular, the present devices and methods relate to removal of the occluding material from the blood vessels as well as other body lumens.

BACKGROUND OF THE INVENTION

The devices and methods of the invention are applicable for various types of intrabody surgery including, but not limited to cutting, breaking, coagulation, vaporization of any body tissue (including but limited to Soft tissue includes tendons, ligaments, fascia, skin, fibrous tissues, fat, and synovial membranes; and muscles, nerves and blood vessels (which are not connective tissue) as well as hard tissue/bone and connective tissue) which involves reaching the targeted tissue through body channels including but limited to blood vessels, ureter, oesophagus, stomach and duodenum (esophagogastroduodenoscopy), small intestine (enteroscopy), large intestine/colon (colonoscopy, sigmoidoscopy) or incision or cut through the body tissues (laparoscopic surgery).

Although devices and methods for removal of the occluding material from the blood vessels as well as other body lumens are discussed below in greater detail, it should be absolutely clear that this is one of many possible applications of the invention. In fact, devices and methods of the invention are applicable to many types of intrabody surgery, as identified above.

Cardiovascular diseases frequently arise from the accumulation of atheromatous material on the inner walls of vascular lumens, particularly arterial lumens of the coronary and other vasculature, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Particular catheter-based interventions include angioplasty, atherectomy, laser ablation, stenting, and the like. For the most part, however, this can be difficult or impossible in tortuous regions of the vasculature. Moreover, the catheters used for these interventions are introduced over a guidewire, and the guidewire is placed across the lesion prior to catheter placement. Initial guidewire placement can be equally difficult if the lesion is total or near total, i.e. the lesion occludes the blood vessel lumen to such an extent that the guidewire cannot be advanced across the lesion.

Occlusion in a blood vessel can be caused by a variety of materials from hard bone like calcium deposits to soft blood clot or piece of fatty deposit. Multiple type occlusions may be present in the same vessel. Currently different tools are used to remove different types of occlusion. Surgeons may need to remove one type of catheter and replace it with another one in order to work with different occlusion types. This extends treatment time, substantially raises cost, and increase risk for a patient. The inventions provide a more optimal and complete solution to this problem which include means to analyze the type of occlusion material present and then adapt the function of the occlusion removal device accordingly. Furthermore, the invention provides a combinational arrangement which enables sergeants to successfully work with different occlusion types without the need to remove one type of catheter/cutting tool and replace it with another one.

In prior art, there are known rotational atherectomy systems utilizing diamond drill tips/burrs to sand-hard calcified occlusions to very small particles. While there are some discussions that the particles produced from 20 μm diamond-tipped burr that ablates plaque into micro-particles are smaller in size (~5 μm) than a red blood cell (8 μm), it is also known that larger particles of debris, produced when occlusion is being broken, are generated. Such larger particles can block blood capillaries and cause serious side effects. However, even when the occlusion particles are as small as blood cells, their presence in the blood stream may present a potential risk. Especially if such particles are accumulated at the essential body tissues, causing malfunctioning of the vital body organs. Visible accumulation of even smaller particles, for example tattoo ink particles (less than 1 μm[9]), is well known. The tattoos particles accumulation (tattoo) is well known to be permanent or at least long term. Since the tattoo ink is inserted into the skin, it mostly stays in the dermis. Thus, impact of the ink particles on other tissue and organs is localized. On the other hand, since the particles generated during the occlusion destruction can be carried out through the blood stream to the vital body organs, proper management of such become important. Some of the rotational atherectomy catheters have built-in arrangements with active aspiration to remove debris from the blood stream and evacuate the debris through the catheter. However, these aspiration (debris evacuation) arrangements are not optimally designed to remove all or most of such debris particles. The inventions propose more optimal and complete solutions to this problem.

The prior art solutions for removal of calcium plaque are often provided with forwardly shaped rotational drills. Such design presents a risk of accidental perforation of the blood vessel walls if such drill is pushed against the wall during the procedure. One of the aspects of the invention provides ways to limit such risks of vessel wall perforation as well as minimizes negative aspects of the procedure on any adjacent tissue.

BRIEF DESCRIPTION OF THE DRAWINGS

In the following drawings, the same parts in the various views are afforded the same reference designators. Referring now to the drawings which are provided to illustrate and not to limit the invention, wherein.

DETAILED DESCRIPTION OF THE INVENTION

As used herein in the description of various components, "proximal" refers to a direction toward the system controls and the operator, and "distal" refers to the direction away from the system controls and the operator and toward a terminal end of the cutter assembly.

In general, the material removal system of the present invention comprises a control unit attached to one end of a catheter assembly and an axially translatable, rotatable drive shaft, with a cutter assembly positioned at the distal end of the drive shaft at least partially supported by the guidewire. The material removal system of the invention further comprises multiple sensors positioned at the cutter assembly area and along the length of the catheter. In one embodiment the system includes wires associated with sensors to deliver electric power to ultrasound or RF emitters.

The cutter assembly is translated over a guidewire to the material removal site and is actuated at the material removal site to cut, grind or ablate, or otherwise remove, the occlusive material. The control unit, and manifold assembly remain outside the body during a material removal operation.

Figure 1:
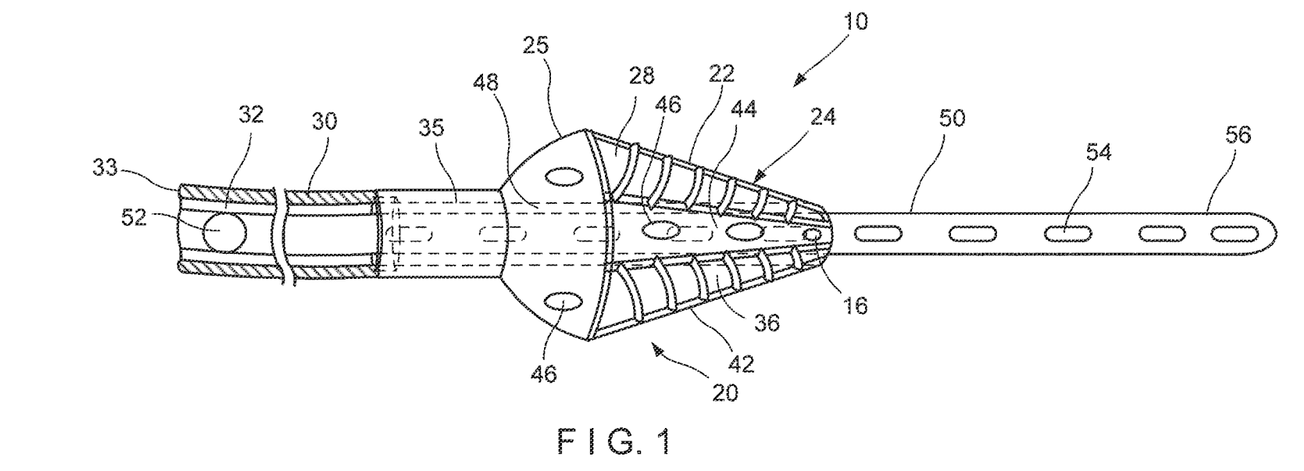
FIG. 1 is a diagram illustrating a burr or cutting tool according to one embodiment of the invention.
Figure 1A:
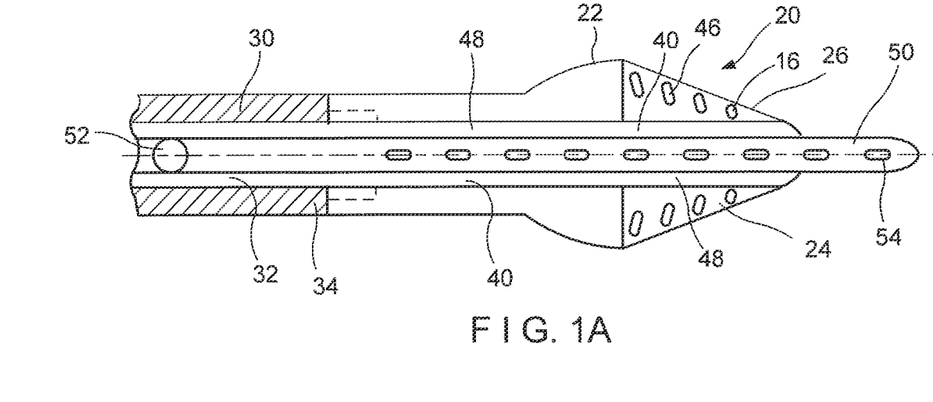
FIG. 1A is a diagram further illustrating of the embodiment shown in FIG. 1.

We are referring now to FIG. 1 illustrating a catheter assembly 10 of one embodiment of the invention provided for passing a high-rotational-speed burr/cutter 20 into blood vessels as well as to other bodily cavities and adapted to ablate and remove abnormal occlusions and deposits. The, burr/cutter 20 actuated by a driveshaft 30 and guided through the vessel to the application area by the guidewire 50, drills away the occlusions in the blood vessel.

The flexible guidewire 50 is navigated through one or more lumens such as blood vessels, to a desired material removal site. The catheter assembly 10 generally houses the burr/cutter 20, drive shaft 30, which also defines a lumen 32 for the aspiration and/or infusion of fluids. It will be also discussed in the application that a gap between a protective sheath of the catheter and the drive shaft is utilized for the aspiration and/or infusion of fluids. The catheter assembly 10 may be fixed to and advanced in concert with the drive shaft 30 to actuate a cutter assembly. The guidewire 50 and the catheter assembly 10 are introduced into a lumen of a patient and navigated or guided to the site of the desired material removal operation.

A proximal end 33 of the drive shaft is operably connected to vacuum or infusion pumps, while a distal end 34 of the drive shaft is operably connected to cutter/burr 20. Drive shaft 30 is preferably a flexible, hollow, helical, torque-transmitting shaft.

The burr/cutter 20 is formed having teardrop-shaped head 22 with a front diamond tipped working potion/surface 24 facing the occlusion and a rear portion. A cylindrical connecting element 35 extends from the rear portion in the proximal direction for connection to the distal end of the catheter. As will be discussed later in the application, optionally a stop member 37 can be provided at the proximal end of the connecting element.

The head 20 is formed with a plurality of cutting flutes 36 and a plurality of ports 46 providing for aspiration and/or infusion. As illustrated in FIG. 1, the burr/cutter has a central bore 40 that is larger than outer diameter of the guidewire 50, so that drive shaft 30 with the cutter 20 are slidable and easily translatable over guidewire 50. The cutting flutes/grooves 36 are formed with sharp blades 42 along the edges defining outer cutting surfaces. Cutting flutes 36 may have sharpened edges to provide cutting and ablation. The cutting edges are arranged to direct debris produced during the cutting operation the inferior the head 20 through the respective ports. Cutting flutes 36 may, additionally or alternatively, have an abrasive or cutting material bonded to one or more surfaces. A distal end portion 26 of the cutter/burr, may additionally or alternatively be provided with abrasive or cutting material. Material such as diamond grit is an example of suitable abrasive.

In one embodiment of the invention at least two cutting flutes 36 are arranged in a radially symmetrical configuration. In another embodiment at least one cutting flute is asymmetrically arranged regarding a longitudinal axis of the head 22.

Cutting flutes 36 are separated from one another by depressions 44 formed with multiple ports 46 providing passage of debris from the exterior of cutter/burr to the central bore 40 forming an internal cavity 48.

The central bore 40 forming the internal cavity 48 extends longitudinally/along a longitudinal axis passing through the central part of the burr/cutter body and is adapted to movably receive the guide wire 50. The cutter/burr 20 is mounted at the distal end 34 of a flexible drive shaft 30 which transmits torque from a torque-generating device, such as an electric or pneumatic motor. The drive shaft 30 is guided by and surrounds a substantial portion of the hollow guidewire 50.

In the preferred embodiment ports/openings 46 are formed within the front portion 24 of the cutter/burr passing through its body, to provide communication/passage between the exterior surface and the internal cavity 48. More specifically, the ports/openings 46 provide communication between the cutting exterior surface 28 engaging the occlusion with the internal cavity 48 and also provide communication with the apertures/ports 54 of the guide wire 50 disposed within the cavity 48.

Particles resulted from operation of the burr/cutter 20 are properly removed to prevent penetration of the particles into a blood stream passing through the vessel. Debris particles resulted from operation of the burr/cutter 20 are drawn through the ports 46 into internal cavity 48 by low pressure zone created in internal cavity by the vacuum pump connected to the distal end of the drive shaft. The ports 46 also allow debris produced during the operation of the burr 20 to be aspirated into the ports 54 in the guide wire. It will be discussed in greater detail below that the guide wire 50 made as a hollow tubular structure is also used as a suction/aspiration conduit for aspiration of occlusion debris produced, as the burr/cutter 20 drills away the occlusion. In an alternate embodiment, the ports 46 can be also provided within the rear portion 25 of the burr. The guide wire can be removed after the burr/cutter 20 is guided within the body lumen to the occlusion. Thus, the entire internal cavity 48 of the burr and the lumen 32 of the shaft can be used for aspiration purposes.

The front working potion/surface 24 of the cuter facing the occlusion may have coatings on its inside or outside for various purposes, for example, for protection against corrosion by body fluids or for insulation against the high energy emitted towards its distal region. It can be of any dimension convenient for its intended use.

Additional structures at the front working potion/surface 24 may help prevent clogging of the suction conduit. For example, a filter, a screen, a mesh, a shield or other barriers can be provided at the distal region of the suction conduit.

In one embodiment of the invention the guidewire 50 is formed as a hollow tube. The drive shaft 30 is also hollow. The particle-entrained blood can flow from the burr 20 through the fluid ports 46 into the bore 40 and interior cavity 48 facing the guide wire 50 which is at least partially disposed within the hollow drive shaft 30 connected to a suction or injection devices.

The hollow tube or central passage 52 of the guide wire 50 is used as a conduit for aspiration of occlusion debris. As illustrated, the guidewire 50 includes a plurality of openings/ports 54 along its distal end 56. Use of such hollow guide wire enables a clinician to catch occlusion debris more efficiently. This is because, the openings/ports 54 allow to catch/collect debris right at the site, where they are produced in the surgical procedure and before being disbursed. The hollow guidewire 50 can be made from metal, or plastic, or grafine or any other material which meets requirement for guide wire and is not permutable for liquid that contains debris of occlusion or embolus.

The hollow/tubular guidewire 50 if needed, is also capable of delivering fluid/medication/coolant to a target location. With ports 54 liquid/fluid/medication is allowed to leak from the hollow passage 52 out into the vasculature passageway. The location of discharge of liquid/medication/coolant from the tubular guide wire 50 can be controlled by controlling size of the openings/ports 54 as well as the location thereof. In addition, a resilient/polymer sleeve may be inserted in the lumen or bore of a tubular guide wire, and/or on the outside as well, for sealing and preventing the outflow or discharge of liquid/fluid/medication from the guide wire lumen. Controlling the length of such sleeves on the guide wire 50 enables control of discharge points of liquid/medication/coolant from the guide wire. Furthermore, the exterior sleeve also provides better engagement/seal between the wire and the interior of vasculature, to assure proper position of a catheter inside the lumen walls. The space between the drive shaft and protective sheath may be also used to receive and deliver lubrication/cooling/medication liquids.

Further important functionality of the ports 54 of the hollow guide wire 50 will become applicable when used in combination with the ports 46 formed in the cutting burr 20.

As to the aspiration aspect of the invention, a vacuum pump 70 (see FIG. 2) creates a low-pressure zone at the proximal end 33 of the drive shaft and the hollow guide wire and/or to aspirate debris of occlusion or embolus in the blood vessel or body lumen produced by the ablation tip.

Controllable entry of the cutter/burr 20 into calcified occlusions/obstructive lesion has to be assured for its predictable advancement. Thus, to facilitate such cutting tool advancement, the drive shaft 30 should be axially translatable with respect to guide wire 50. In the current prior art practice to initiate evacuation of residual debris. In this often complicated and time-consuming technique/procedure, the tool similar to the burr/cutter 20 is nudged into a calcified occlusions area during rotation and then retracted. This manipulation in the prior art procedure permits evacuation of residual debris and to reestablish local circulation before making another cutting cycle on the lesion. On the other hand, in the present invention the ports 46 in the body of the burr/cutter 20 establish a reliable communication between the burr cutting blades 42, the hollow passage 52, and the ports 54 of the guidewire. In this manner residual debris are evacuated continuously during the procedure without the need for the complicated manipulations discussed above.

Although the cutter/burr 20 has been discussed above for the removal of the occluding material from the blood vessels, it should be noted that application of the burr to many types of the intrabody surgery (as identified above) also forms a part of the invention. For example, in the ureteroscopy procedure, which treats and removes stones in the kidneys and ureters, the burr 20 may be used in combination with the respective flexible scope. In the procedure doctor passes the scope with the burr through patient bladder and ureter into kidney. Use of the burr 20 may be especially applicable for larger stone removal and can be combined with other techniques and/or tools including energy-based devices to break stones up. Use of the burr 20 may be also applicable in the ureteroscopy for the removal of polyps, tumors or abnormal tissue from a urinary tract. Further application of the burr 20 is in percutaneous nephrolithotomy or percutaneous nephrolithotripsy, combined with a small tube to reach the stone, the burr grinds/breaks the stone up. This action can be combined with the use of high-frequency sound waves, radio frequency or other energy-based devices. After the procedure the pieces of a stone are vacuumed up and removed from the system with a suction arrangement of the invention.

Figure 2:
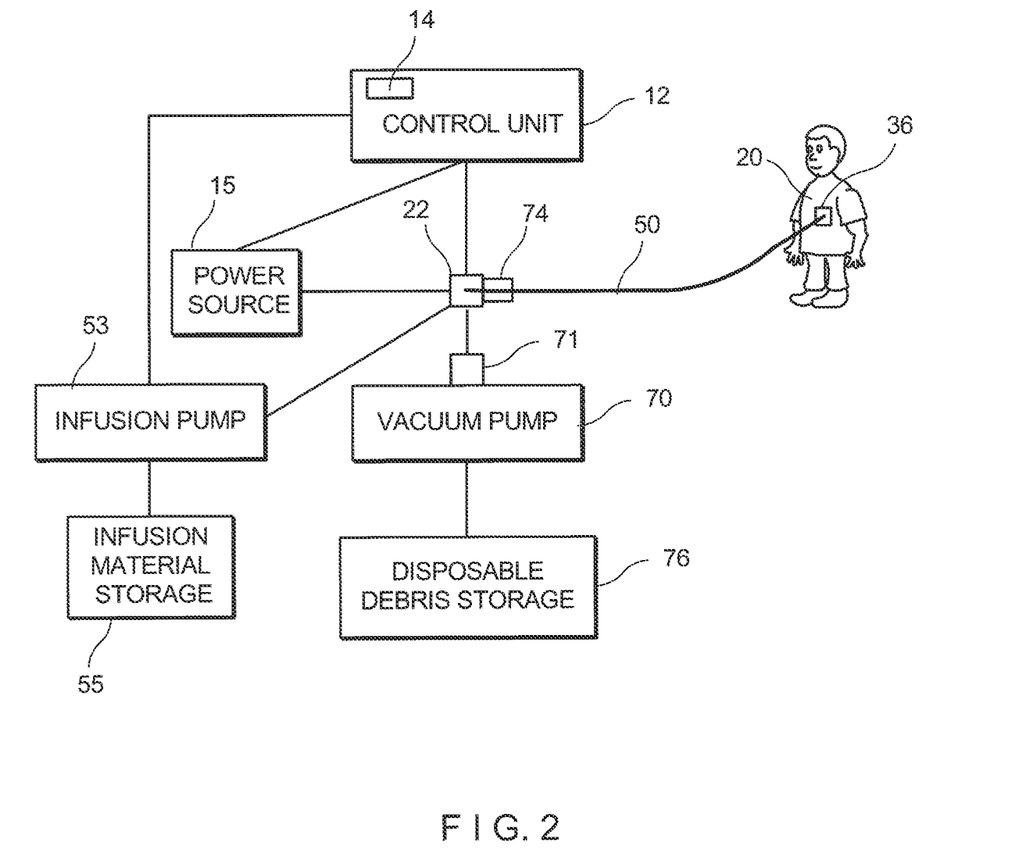
FIG. 2 is a diagram illustrating the system of the invention.

The control unit 12 preferably comprises a base arranged so that the control unit may be stably supported on a work surface or a body surface during material removal operations. The control unit 12 also preferably incorporates control systems for actuating, adjusting and providing system information concerning power, drive shaft rpm, drive shaft axial translation, aspiration, infusion and the like.

As illustrated in FIG. 2 the control unit 12 houses a programmable logic controller and power source 15 in operable communication to provide power and to control operation of various units of the system of the invention. The control unit may include, but not limited to vacuum control unit, cutter advancer unit, guidewire control unit, cutter assembly drive control, and aspiration and infusion control unit. The control unit 12 also controls a block providing information concerning operating conditions and feedback from the material removal site to the operator. According to one embodiment, control unit 12 utilizes inputs received from multiple sensors 16 located at the burr/cutter 20 and/or other critical regions of the catheter assembly to continuously updated output to an operator including such operating parameters as temperature at the material removal site; cutter assembly rotation rate and/or advance rate; aspiration rate and/or volume; infusion rate and/or volume; and the like. Control unit 12 may additionally provide adjustable controls permitting the operator to control operating parameters of the cutter assembly and material removal operation.

As illustrated in FIG. 2, the control unit 12 is provided to regulate the energy/power source 15 for the optimum output level based on type and characteristics of the targeted occlusion (hard, soft, blood, etc.) and/or characteristics of the burr catheter (length, diameter, temperature, etc.). Characteristics of the control unit 12 may be adjusted by the operator or automatically based on inputs from the sensors 16. Controlling various characteristics/parameters at the operation cite are based on the information provided by sensors positioned at the distal end of the catheter and the burr, such as for example speed of rotation, temperature, etc.

Such characteristics can be manually or automatically adjusted based on the signals and data received from the sensors 16 installed within the cutter/burr 20.

Detectors/Sensors 16, 18 may emit and receive various types of signals (optical, electromagnetic, acoustical, capacitance measuring) that will change parameters depending on the composition or other physical properties of the occlusion and/or tissue surrounding occlusion and/or physical characteristics of the catheter itself, so as to allow the control unit 12 to calculate and generate proper signals controlling operation/speed of rotation, etc. of the burr 20.

Detectors/Sensors 16 located at the distal end of the burr 20 are able to recognize (determine) the physical and chemical properties of the occlusion. A computer or microchip 14 associated with the control unit 12 receives and analyzes information/data obtained by the sensors and generates signals to adjust parameters of the power source to optimize the destruction of an occlusion in the blood vessel and/or to produce other desired effect on targeted soft tissue. As an example, the control unit 12 analyzes information/data obtained by the sensors and generates signals to adjust parameters of the power source to optimize rotational speed, etc. of the burr 20.

According to one embodiment of the invention, sensors 16 are capable of detecting the level of hardiness/calcification, water/moisture content, etc., within the material of an occlusion. As the burr 20 passes through various zones/sections/areas of the occlusion, optimal levels of rotational speed, etc. can be achieved for each zone of treatment. For example, a higher speed of rotation can be provided for the destruction of calcinated occlusion having higher degree of hardiness. On the other hand, lower speed will be generated for the areas with softer occlusion materials.

Utilization of the cutting burr 20 of the invention is also accompanied by automatic target feedback, thermal feedback for example, to precisely control the speed of rotation, etc. This is needed to prevent damage to surrounding tissue. For this purpose, non-contact thermal detectors 17 can be provided. The output of the non-contact, thermal detectors 17 can be used to adjust the output of the power source 15 to maintain selected characteristics including temperature at the treatment site.

In the invention to effectively control the destruction of the occlusion, a condition of the entire artery body and/or the tissue surrounding the operation site is monitored by the detector 17 adopted to detect irradiation reflected from such tissue. One of the essential functions of the detector 17 is to control the effect of the drilling/ablation on the tissue surrounding the site. In every individual case, a doctor sets specific rotational, etc. characteristics to produce the required effect. If a situation at the operation site becomes unfavorable, for example the temperature exceeds predetermined limits, the detector 17 generates a signal directed to the control unit 80, which in turn produces a correcting signal to the power source 15 or to the control unit 12.

The computer or microchip 14 of the control unit 12 receives and analyzes the information obtained by the detector 17 and to generate a control signal to adjust parameters of the power source 15 in such a way as to optimize the destruction of an occlusion in the blood vessel or other desired effect on targeted soft tissue.

In an alternate embodiment the control signal generated by the thermal detector 17 energizes the cooling arrangement (see above) to directly or indirectly lower/adjust temperature at the site. This is necessary to exclude possibility of damaging an adjacent tissue. The detector 17 and the sensors 16 can be made utilizing a wide variety of photoelements, photoresistors, photodiodes and similar devices.

As discussed above, frictional forces resulted from the engagement/drilling between the burr 20 and the material of the occlusion, as well as other factors may result in temperature elevation of the surrounding tissue. In the invention, the temperature elevation occurs controllably without causing irreversible thermal damage to the surrounding tissue of the arteries. The control unit 12 adjusts the energy to maintain a pre-selected target temperature at the site/spot. In one embodiment of the invention, to maximize patient safety, an optional continuous or pulsed cooling device can be provided to deliver a coolant from the infusion material storage 55 by means of the infusion pump 53 through the hollow guide wire 50 to the operation site during or after the surgical procedure.

The diagram of FIG. 2 schematically depicts a system according to one embodiment of the present invention that may be connected to the cutter 20 to evacuate the ablated or cored bodily material from a subject's vascular system using various embodiments of the cutter/burr 20. The vacuum pump 70 provided at the proximal end of the system creates a low-pressure zone resulted in suction pressure within the hollow inner space of the drive shaft and the guide wire 50 to evacuate cut and/or ablated bodily material directly from the operating site in the vascular system.

In another embodiment, the vacuum pump 70 is interconnected to a pulse modulator 71, the actuation of which creates one or more pressure differentials to the aspiration system. Accordingly, in this embodiment rather than creating a constant suction pressure within the system to evacuate cut and/or ablated bodily material from a subject's vascular system, the aspiration system of the invention applies alternative pressure(s), thereby creating pulses of suction pressure within the lumen. Utilizing a series of constant and/or varying pressure pulses is potentially beneficial in aspirating bodily material, particularly when aspirating larger cylindrically looking core or plug like shapes of bodily material.

Aspirated liquid and/or particle from an area near distal end of the tool are accumulated and stored in the disposable debris storage 76. A filter 74 can be also provided upstream of system for filtering debris and aspirated bodily material and also for providing visual feedback to a user related to the type, quantity, and flow rate of material being removed from a patient. The debris collection container 76 may be in fluid communications with the vacuum pump 70 and may include one or more known devices for collecting and filtering materials removed from a patient. The container 76 may have transparent sidewalls for providing visual feedback to a user regarding flow-rate, content, coloration, etc. Those of skill in the art will appreciate that various types of collection containers may be used. The collection container 76 and/or filter 74 may also comprise one or more custom filter features with various mesh sizes, capacities, etc. based on the specific application.

The distal end 56 of the hollow guide wire 50 functioning as a suction conduit can be made of a variety of flexible or rigid materials or a combination of both, such as stainless steel or plastics. Still further, the distal end 56 of the guide wire formed as a suction conduit can be made of a material different from the body of the hollow guidewire. For example, one might want to make the distal end 56 with a more heat-resistant material to withstand high energy directed to it. It may also be desirable to use a more impact-resistant material to withstand the initial impact from the solid particles drawn by the suction force.

Figure 3:
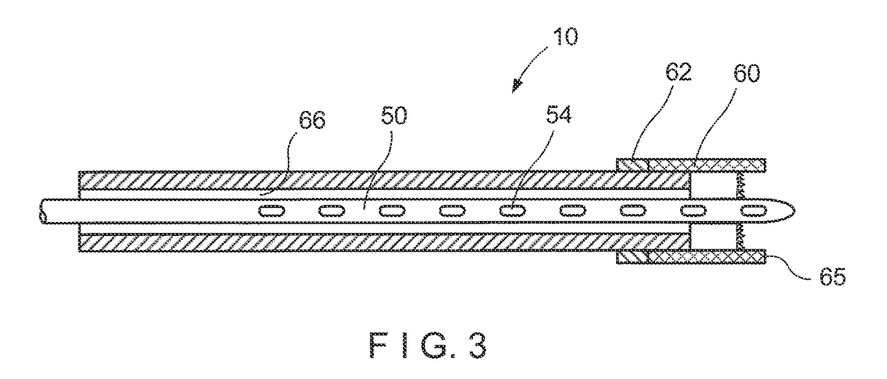
FIG. 3 illustrates a distal end of a catheter including a slidable sleeve in an extended position according to another embodiment of the invention.

We are referring now to FIG. 3, showing an expanded/working position of a sliding sleeve 60 according to another embodiment of the invention. As illustrated, the distal end of the catheter assembly 10 is provided with the sliding sleeve 60 having an activating mechanism 62 provided for controllable movement of the sleeve back and forth along the catheter. In one embodiment of the invention the activating mechanism 62 is spring controlled. However, the activating mechanism 62 can be energized/actuated in any conventional manner, such as for example electrical, pneumatic, etc. mechanisms are contemplated. The front, distal end 65 of the sleeve 60 is designed to arrange a tight contact between the catheter and the occlusion. This significantly enhances catching the occlusion debris and channeling them into the hollow tubular passage 66 for aspiration. As illustrated, in the expanded working position the sleeve 60 extends outwardly from the exterior surface of the catheter 10. In this arrangement the diameter of the outer periphery at the distal end of the catheter is slightly increased. In the contracted position the sleeve 60 is positioned along the exterior surface of the catheter.

Figure 4:
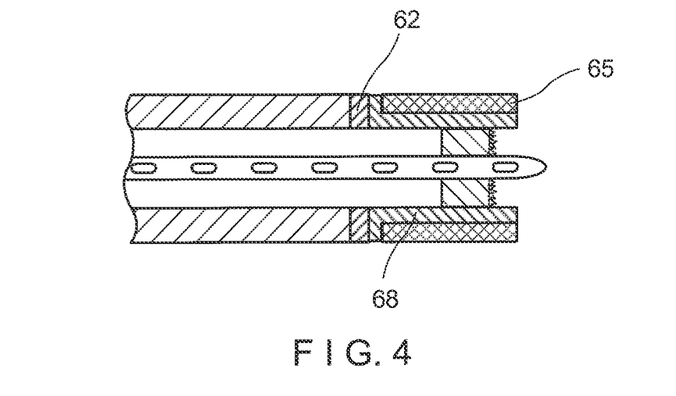
FIG. 4 illustrates the slidable sleeve in a retracted position according to a further embodiment of the invention.

In another embodiment, illustrated in FIG. 4, a circumferential recess 68 is formed within the distal end of the catheter body having the depth and length corresponding to the respective dimensions of the sleeve 60. In this embodiment the exterior surface of the sleeve is in flash with the exterior surface of the catheter. Prior to the catheter's placement through the blood vessel lumen to the operation site, the sleeve 60 is pressed inwardly in the direction of the proximal end to overcome resistance of the activating mechanism 62. As a result, the sleeve 60 is submerged within the circumferential recess 68. In this locked position the exterior of the sleeve 60 is in flash with the exterior of the catheter. Upon delivery and proper positioning at the site, the activating mechanism 62 is released-unlocked and the sleeve 60 is moved to the expanded working position to provide a tighter contact between the distal end 65 of the sleeve 60 and the occlusion. The engaging distal end 65 of the sleeve 60 can be made of a resilient or soft material capable of adopting evolving configuration of the external part of the occlusion during the procedure.

Figure 5:
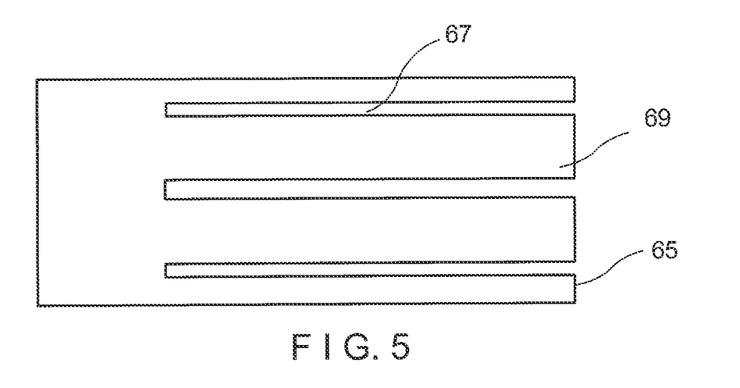
FIG. 5 illustrates another embodiment of the slidable sleeve.

In an alternate embodiment, to further increase resiliency of the sleeve, as illustrated in FIG. 5, longitudinal slits 67 are circumferentially arranged within the sleeve body. The slits 67 extend inwardly from the distal end of the sleeve to separate the sleeve body into a plurality of segments 69. In one embodiment of the invention distal area of the segments 69 can be curved and/or formed from a resilient material to further improve engagement with the occlusion. Any reasonable number and configuration of the slits are within the scope of the invention.

Figure 11:
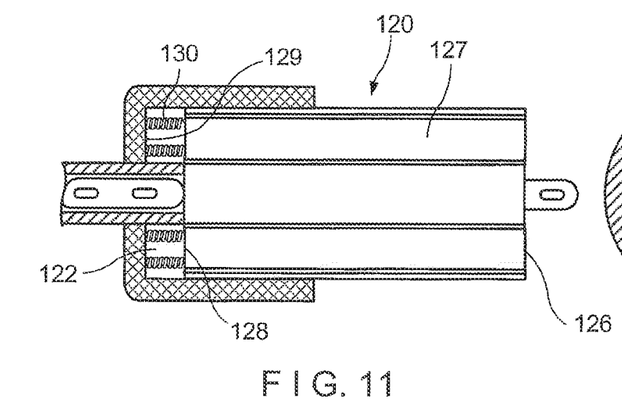
FIG. 11 is a view of a modified embodiment showing the slidable sleeve.
Figure 12:
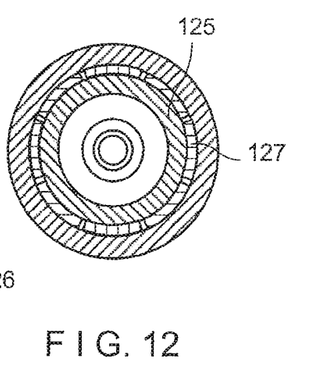
FIG. 12 is a section view of the embodiment shown in FIG. 11.

Turning now to FIGS. 11 and 12 showing another embodiment of a sleeve assembly 120 which consists of an external base 122 and an internal support 125 spaced from each other by a receiving gap 131. A plurality of separated from each other engaging segments 127 are positioned in the receiving gap 131 for independent slidable movement along a longitudinal axis. The base is formed with an inner cavity 122 extending forwardly from a rear wall 129 and is adapted to slidably receive the plurality of the engaging segments 127. Any reasonable number of the segments symmetrically positioned along its longitudinal axis is contemplated. Each engaging segment consists of at least a front part 126 adapted for engagement with an occlusion and a rear part 128 adapted for slidable movement within the inner cavity 122. Each segment 127 slides within the inner cavity 122 along the longitudinal axis of the sleeve independently from other segments. A biasing member or a spring 130 is positioned between the rear end of each segment and the rear wall of the base. Thus, upon the sleeve approaching the occlusion, the front parts of each segment which is pressed by the biasing member, engages a specific configuration of the respective area of the occlusion independently from other segments. The engaging distal end of each segment can be made of are resilient or soft material. In this embodiment the front parts 126 of independently movable segments are capable of adopting evolving configuration of the external part of the occlusion. Therefore, the sleeve assembly provides an improved tighter contact between the front parts of the segments and the occlusion during the procedure.

Figure 6:
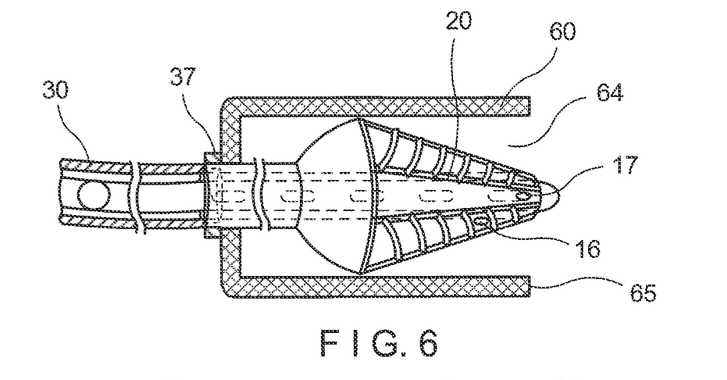
FIG. 6 is a diagram illustrating one position of the embodiment combining the burr and the slidable sleeve.

FIG. 6 illustrates yet another embodiment of the present invention which combines application of the above-discussed burr/cutter 20 with the sliding sleeve 60 movably positioned at the rear portion of the burr, which is connected to the distal end of catheter 10. As illustrated, the sleeve 60 is moved proximally and is prevented from further motion in this direction by a stop 37 provided at the at the rear cylindrical portion of the burr. The hollow interior of the sleeve defines an interior space 64 that serves as a burr/cutter housing. As shown in FIG. 6 the cutter/burr 20 resides in the interior space 64 when axially retracted in a proximal direction when the cutting procedure is completed.

Figure 7:
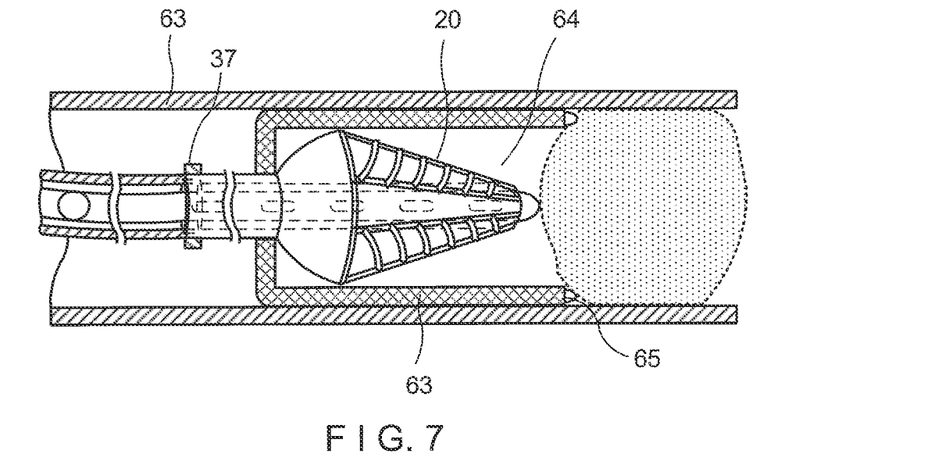
FIG. 7 is a diagram illustrating another position of the embodiment shown in FIG. 6.

A further position of this embodiment is illustrated in FIG. 7, depicting that the sleeve 60 is moved away from the stop 37 distally to the expanded position and a tight contact between the distal end 65 of the sleeve and the occlusion is assured. An abrasive or cutting material is bonded or by any other conventional means attached to the distal end 65 of the sleeve, forming an auxiliary cutting region. In an alternate embodiment, a cutting element or a cutting edge can be formed instead of the abrasive material. In this manner this embodiment is formed with two cutting regions, including the burr/cutter 20 and the auxiliary cutting region.

By the motion of the catheter the burr/cutter 20 is delivered through the interior space 64 to the operation site. In this manner, the cutting tip of the cutter/burr 20 is positioned at a (predetermined) area of the occlusion, followed by the cutting process with the burr 20 being rotated by the drive shaft 30.

Figure 7A:
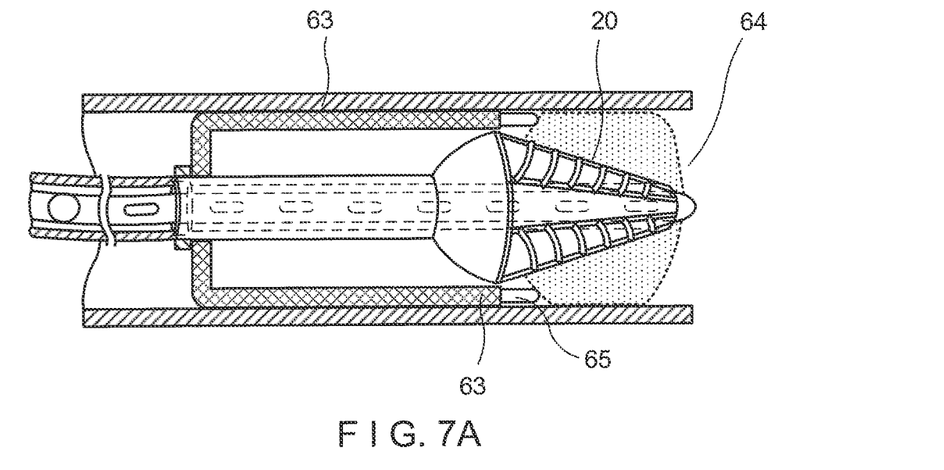
FIG. 7A is a diagram illustrating a further position of the embodiment shown in FIG. 7.

Turning now to FIG. 7A illustrating a further step in operation of this embodiment. In the cutting process, to drill away the occlusion the rotating burr 20 is moved by sliding the catheter in the distal direction until the stop engages the rear face of the sleeve. Upon this engagement a locking device locks the sleeve at the rear portion of the sleeve, so that combined/mutual rotation of the sleeve and the cutting burr 20 is initiated. In this process a major central portion of the occlusion is cut or drilled away by the cutting burr 20. However, in the prior art a portion of the occlusion along inner walls of the blood vessel or lumen is not removed due to relatively small outer diameter of the burr. In the invention, as illustrated in FIG. 7A this part of the occlusion is removed or cut away by an auxiliary cutting region formed at the distal end 65 of the rotating sleeve. Thus, application of this embodiment enables a practitioner to eliminate or cut away the entire occlusion in one procedural step.

Furthermore, during the cutting procedure, walls of the sleeve 60 separate/isolate the cutter 20 from the blood vessel walls 63. Thus, a risk of accidental perforation of the blood vessel walls 63 or any other adjacent tissue during the procedure is minimized. The interior space 64 of the sleeve creates a conduit which accommodates materials cut during the procedure and improves the flow of various fluids during aspiration and/or infusion.

It should be noted that application of the slidable sleeve 60 is not limited to the removal of the occluding material from the blood vessels. The sleeve 60 can be used in many types of the intrabody surgery (as identified above). For example, it can be used in ureteroscopy procedure, which treats and removes stones in the kidneys and ureters. The sleeve 60 may be used in combination with the flexible scope, which is passed through patient bladder and ureter to provide an enhanced contact with kidney. Use of the sleeve 60 facilitates larger stone removal, combined with a laser, which passes through the scope to break stones up. Another example is use of the expandable sleeve 60 in the ureteroscopy for the removal of polyps, tumors or abnormal tissue from a urinary tract. Similar to the above discussed manner, the sleeve 60 can be used in percutaneous nephrolithotomy or percutaneous nephrolithotripsy, combined with a small tube to reach the stone and break stone up with high-frequency sound waves or a laser. The broken pieces are vacuumed up and removed from the system by a suction arrangement of the invention.

Although an assembly combining the burr/cutter 20 with the sliding sleeve 60 has been discussed above, it should be noted that use of the cutter with other type pf protective devises is within the scope of the invention. For example, an assembly where the burr/cutter 20 is combined with the sleeve arrangement illustrated in FIGS. 11 and 12 is also contemplated.

Figure 8:
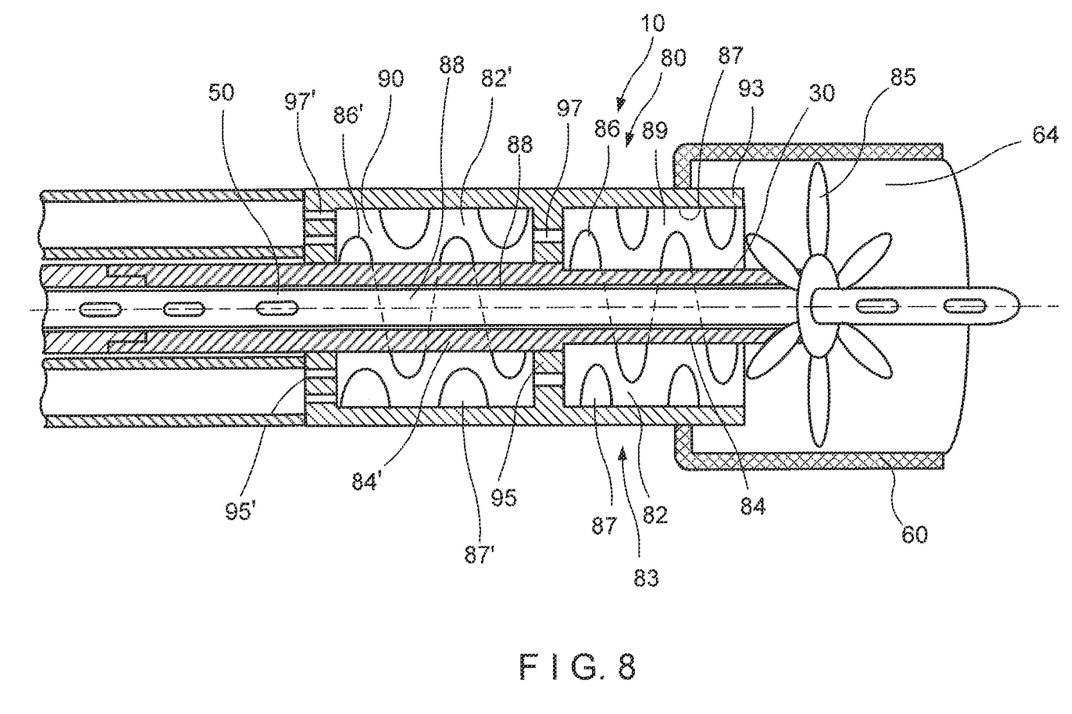
FIG. 8 illustrates an embodiment of the invention including a rotatable blade.

In a further embodiment of the invention illustrated in FIG. 8, a processing unit 80 with a rotatable blade or cutting element 85 is provided at the distal end of the drive shaft 30 to cut and macerate the occlusion (embolus) and direct/evacuate cut materials away from the site.

The processing unit 80 comprises a chamber 82 rotatably receiving a drive shaft assembly 84 having a conveying member 86 rotationally positioned thereinside. The conveying member 86 is adapted to receive the occlusion material cut by the cutting element 85 and then to transport the material along the chamber 82.

In the illustrated embodiment, the drive shaft assembly 84 both transports removed or cut tissue in the processing unit 80 and drives rotation of the cutting element 85. In other embodiments the drive shaft 84 may transport removed or cut tissue proximally within the processing unit 80 but may not drive rotation of a cutting element 85. FIG. 8 shows that the drive shaft assembly 84 is attached to the cutting element 85.

The drive shaft 84 is generally cylindrical and may comprise a solid tube or a hollow tube. The drive shaft with the conveying member 86 is manufactured to be flexible enough to facilitate navigate navigation through tortuous vessel anatomy and strong enough to withstand the stresses encountered by high speed rotation, transmission of torque through the driveshaft to the cutter 85 at the distal tip of the processing unit 80, and transport of calcified material. The conveying member 86 may be a separate element which is attached or affixed in some manner to a substantially cylindrical drive shaft. Alternatively, the drive shaft 84 and the conveying member 86 may be formed as a single unitary element.

The drive shaft 84 is formed having a central lumen 88. Since the lumen 88 is used to deliver the guidewire 50, it may be coated with a lubricious material or made of a lubricious material to avoid binding with the guidewire. The central lumen 88 of the shaft 84 may also be used to deliver fluids to the operative site simultaneously with the guidewire or in place of the guidewire.

In one embodiment of the invention a plate 95 having a plurality of holes 97 passing from one face of the plate to the other is positioned within the chamber 82 transversely to the longitudinal axis thereof. In this manner, the occlusion material initially cut by the cutting member 85 is delivered by the conveying member 86 to the chamber 82 for further processing by passing through the plurality of holes 97 of the plate 95. Use of the plate 95 having the plurality of holes 97 is recommended where highly calcified occlusion is treated by the apparatus of the invention. The receiving chamber 82 along with the shaft 84 with the conveying member 86, and the optional plate 97 forms a first processing section 83 of the unit 80.

The conveying member 86 may be an auger type system or an Archimedes-type screw that conveys the debris and material generated during the procedure away from the operative site. The conveying member 86 has a raised surface or blade that drives materials away from the operative site.

Debris can be evacuated outside the body by the conveying member 86 action along the length of the catheter and with or without supplement of the vacuum pump connected to the catheter. Alternatively, the debris may be accumulated in a reservoir within the device.

Optionally, a plurality of generally equally spaced ridges 87, which can be collapsible in nature, can be provided, extending from an inner wall 89 of the chamber. The ridges 87 tend to provide sufficient clearance about the conveying member 86. In this manner, initially processed occlusion materials can be propelled through the processing unit 80 without development of back pressure due to clogging in the assembly. The ridges 87 are aligned to increase material throughput rate by channeling material towards the distal end of the unit 80.

As illustrated in FIG. 8, optionally the tool of the invention can be provided with a second processing section 90. The second section 90 comprises a second chamber 82' with a second drive shaft 84' having a conveying member 86' with a second pitch generally somewhat smaller than the pitch of the first conveying member 86. The first and second conveying members are co-axially arranged and formed with a longitudinally extending apertures used to accommodate, among other functions the hollow guidewire of the invention. The second section 90 can be optionally provided with a second plate 95' having a second plurality of holes 97' passing therethrough from one face thereof to the other. The holes 97' of the second plate 95' are smaller than the holes of the first plurality of holes 97. In this manner, as previously discussed, the occlusion materials are initially processed/ground by passage through the first plurality of holes 97 under the impetus of the first conveying member 86. Then, such initially processed/ground material is further processed/ground to a smaller size by passage through the second plurality of holes 97' under the impetus of the second conveying member 86'.

The second processing chamber can be employed in certain situations, for example, where highly calcified occlusion is encountered. In this instance, the material exiting the first plurality of holes can be in the form of relatively coarse agglomerations. Such material is then picked up and propelled by the second screw and the plurality of ridges, so as to help to guide the material towards the second plate. As the material passes through the second plurality of holes of the second plate, further reduction of sizes of the occlusion particles takes place.

As illustrated in FIG. 8 the processing unit 80 can be optionally provided with the sleeve 60 slidably arranged at the exterior part of its body. In the illustrated expanded position, the sleeve 60 extends outwardly from the distal end of the unit 80. The hollow interior of the sleeve forms an interior space 64 that serves as a housing of the cutting element 85. More specifically, the interior space 64 also accommodates the location where the drive shaft is attached to the cutting element 85. When the sleeve 60 is retracted in the proximal direction, the cutting element 85 is exposed.

In use when the sleeve 60 is in the expanded working position the distal end of the sleeve 60 engages the occlusion, then the drive shaft and the attached cutting element 85 are delivered through the interior space 64 to the operation site. The interior space 64 of the sleeve also creates a conduit which accommodates materials cut during the procedure and to improve the flow of various fluids during aspiration and/or infusion. In this embodiment the cutting element 85 is precisely delivered to the occlusion. Further, the walls of the sleeve isolate the cutting element 85 from inner surfaces of the blood vessel walls, minimizing the risk of accidental perforation/damage of the blood vessel walls during the cutting procedure.

In operation of the processing unit 80, initially the occlusion material cut by the cutting element 85 is processed is fed into the chamber 82. The drive shaft assembly 84 having a conveying member 86 propel the cut occlusion material towards and through the holes in the plate 95. Thus, size of the initially cut occlusion materials is reduced to become more adaptable for suction, collection and disposal as previously discussed. To further reduce the cut occlusion materials the second processing chamber may be utilized in the above-discussed manner.

When light sources 93 are provided at the distal end of the catheter, the cutter 85 is arranged to minimally block the emitted light. Light is pulsed in such a way that it pulses when light outlets 93 are not covered/blocked by cutter 85.

Application of the processing unit 80 combined with the cutting element 85 to many types of the intrabody surgery (as identified above) also forms a part of the invention. For example, in ureteroscopy procedure, which treats and removes stones in the kidneys and ureters, the processing unit 80 may be used in combination with the respective flexible scope. Use of the processing unit 80 is also applicable for larger stone removal, combined with a laser, which passes through the scope to break stones up. Further, in the ureteroscopy the processing unit 80 can be used for the removal of polyps, tumors or abnormal tissue from a urinary tract. The processing unit 80 including the cutting element 85 is also usable in percutaneous nephrolithotomy or percutaneous nephrolithotripsy, combined with a small tube to reach the stone and break stone up with high-frequency sound waves or a laser. After the procedure the pieces are vacuumed up with a suction arrangement of the invention.

Figure 15:
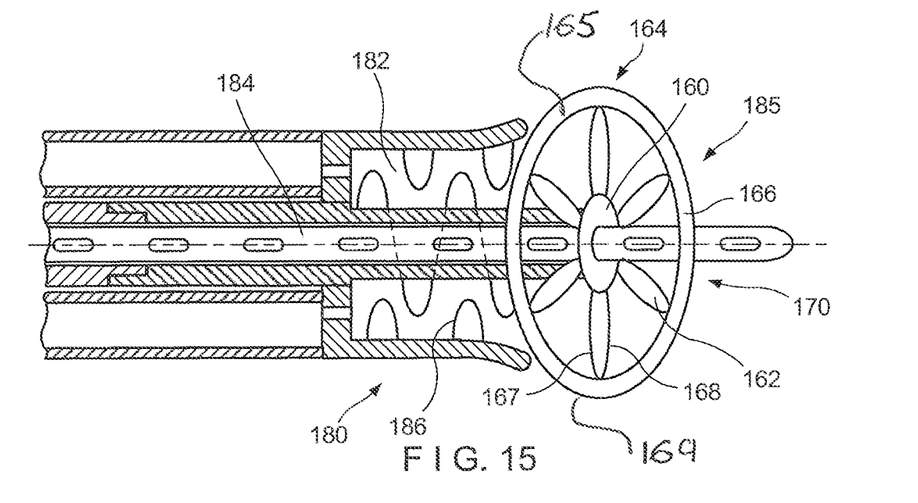
FIG. 15 illustrates an embodiment of the invention utilizing a rotatable blade assembly.

Turning now to FIG. 15 showing a processing unit 180 formed with a rotatable blade assembly 185 is provided at the distal end of the drive shaft 184. The rotatable blade assembly 185 includes a hub 160, a plurality of blades 162 arranged at the hub and an outer band 164 arranged at outer peripheries of the blades 162. In one embodiment, the hub, the blades and the outer band can be integrally formed. Each blade 162 is formed having a leading cutting edge 168 and a trailing edge 167 and extend in a plane generally perpendicular to axis of rotation. The outer hand 164 has a front/distal area 166 facing the occlusion and a rear/proximal area. An abrasive or cutting material is bonded or by any other conventional means attached to the distal area, forming an auxiliary cutting region 170. In the alternative, a cutting element can be formed at the front area 165 of the outer band. Thus, the blade assembly 185 is formed with two cutting regions, including the primary cutting region defied by the leading cutting edges 168 of the blades 162 and an auxiliary cutting region 170 defined the front/proximal area 169 of the outer band. In use upon approaching the occlusion, the leading edges 168 of the primary cutting region remove or cut away a central area of the occlusion. In the prior art procedures due to smaller outside diameter of the cutting tools relative to the inner diameter of the blood vessels and other reasons, an occlusion tissue disposed at the inner surfaces of the blood vessels often remains unremoved. In the present invention this tissue of the occlusion, which is adjacent to the inner walls of the blood vessel, is eliminated or cut away by the auxiliary cutting region 170. Thus, application of the rotatable blade assembly of this embodiment enables a practitioner to eliminate or cut away the entire occlusion in one procedural step. This embodiment can be used for cutting soft occlusions tissues and is particularly adapted for application in stent restenosis procedures.

Similar to the embodiment of FIG. 8, the processing unit 180 includes a chamber 182 having the drive shaft 184 provided with the conveying member 186. The drive shaft and the conveying member both transport removed or cut tissue in the processing unit 180 and drive rotation of the cutting blade assembly 185. As illustrated in FIG. 15, the catheter is formed with an exterior sheath spaced from an inner hollow tube receiving the drive shaft. The drive shaft 184 is formed having the central lumen 188 used to deliver the guidewire 50 and may be also be used to deliver fluids to the operative site. To facilitate rotation of the drive shaft lubricant can be delivered through the space separating the interior of the hollow tube and the drive shaft.

The occlusion material cut by the cutting blade assembly 185 is delivered by the conveying member 186 to the chamber 182 for further processing as previously discussed in the embodiment of FIG. 8. Then debris of processed cut material are evacuated through the space separating the exterior sheath from the inner tube with or without supplement of the vacuum pump connected to the catheter. Alternatively, the debris may be accumulated in a reservoir within the device.

Figure 9:
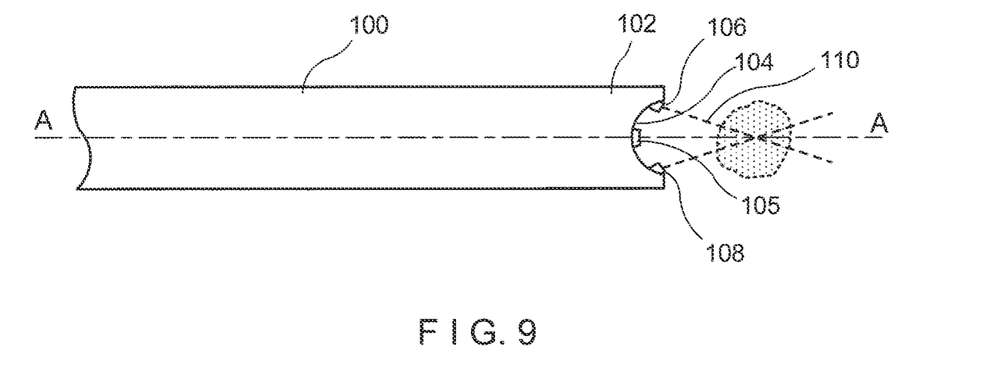
FIG. 9 is a diagram illustrating an embodiment of the invention utilizing ultrasound energy.

Turning now to FIG. 9 illustrating still another embodiment of the invention, wherein a source (generator) of ultrasound energy is disposed at the proximal end of the catheter. In the illustrated embodiment the source is in the form of one pair of spaced from each other ultrasound waive generators provided to generate ultrasound waves/beams focused on a specific area near the proximal tip of the catheter. In use the proximal end is delivered to the occlusion, so that the ultrasound beams are focused within the body of the occlusion for selective destruction of the occlusion tissue. Since the focus is separated/spaced from the surrounding vessels, the risk of collateral damage to surrounding tissue or blood vessels walls is minimized. Although one pair of cooperating ultrasound generators is shown, it should be appreciated however that the distal end of the catheter can be provided with any reasonable number of cooperating ultrasound generators.

As illustrated in FIG. 9, a distal end 102 of the catheter 100 is formed having a convex-shaped region 104 with one pair of the symmetrically arranged ultrasound energy generators 106 and 108. The convex-shaped region 104 reflects the energy emitted from the ultrasound generators. In this embodiment the beams 110 of the ultrasound energy are optimally focused at a specific/predetermined area within the body of the occlusion for a selective destruction of its material/tissue. The focus of the beams 110 is disposed along the longitudinal axis A-A of the catheter and spaced from the distal end 102.

The convex-shaped region 104 may also form a suction cup which facilitates engagement between the distal end 102 of the catheter and the occlusion, so as to prevent spreading and facilitates catching of the debris. In addition to the ultrasound energy generators detector and/or sensors 105 can be provided at the distal end of the catheter. The sensors/detectors detect data related physical and chemical composition of the occlusion tissue and transmit such data to the control unit. The computer or microchip 35 of the control unit 30 receives and analyzes the information obtained by the sensors/detectors 105 and is capable of generating a control signal to adjust functionality of the ultrasound energy generators, so as to optimize the destruction of an occlusion in the blood vessel or other desired effect on targeted soft tissue.

The convex-shaped region 104 of the catheter 100 provided with the ultrasound energy generators is also adaptable for use with the sleeve 60 slidably arranged at the exterior area 114. In the expanded position illustrated in FIG. 10, the hollow interior space 64 of the sleeve 60 serves as a housing for the convex-shaped region 104 accommodating the ultrasound energy generators 106 and 108. In use the sleeve 60 is placed into the expanded into the working position, and the distal end of the catheter with the ultrasound energy generators is delivered through the interior space 64 to the close proximity of the occlusion. In this manner, the ultrasound beams 110 are optimally focused at a specific area at the body of the occlusion for a selective destruction of its material. The interior space 64 of the sleeve 60 forms a conduit which accommodates materials cut during the procedure and improves the flow of various fluids during aspiration and/or infusion. The convex-shaped region 104 with the ultrasound energy generators are precisely delivered to the occlusion, and the walls of the sleeve isolate the generators 106, 108 from inner surfaces of the blood vessel walls 112, minimizing the risk of accidental perforation of the blood vessel walls.

Figure 13:
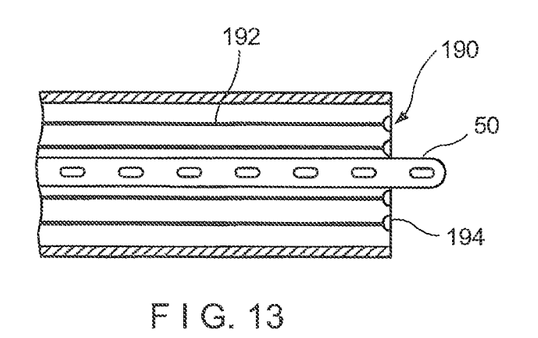
FIGS. 13 and 14 are diagrams illustrating still another embodiment of the invention utilizing RF energy.
Figure 14:
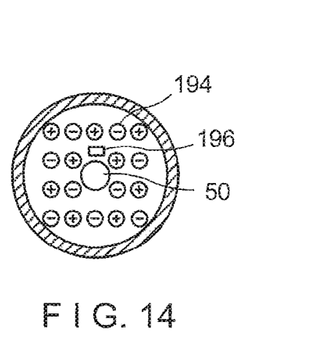

Turning now to FIGS. 13 and 14 illustrating an embodiment of the invention, wherein a source 190 (generator) of RF (radio frequency) energy is disposed at the proximal end of the catheter. As illustrated in FIG. 13 the catheter includes one or multiple electric wires 192 longitudinally extending within a hollow catheter body to deliver electric current/voltage to the RF electrodes 194 positioned at the distal end. In the alternate embodiment the electrodes may be positioned at any place within the body of the catheter between the proximal end and the distant end. In use the RF energy destroys or affects a soft tissue or an organ in a certain desirable way through cutting or coagulating mechanisms or increase of temperature of targeted tissue. One of the advantages of this embodiment is that only thin electric wires 192 are needed to transmit energy to RF electrodes 194 at the distal end of the catheter. Open spaces formed within the catheter body between the wires and/or electrodes are used to evacuate ablated bodily material produced during the procedure. The evacuation can be accomplished, for example by a vacuum pump provided at the proximal end of the system creating a low-pressure zone resulted in suction pressure within the hollow inner space of the catheter, so that ablated bodily material directly removed from the operating site.

RF electrodes are positioned at the distal end, so that the electric current alternating between electrodes destroys the occlusion located between the electrodes efficiently covering the surface of the occlusion. Because RF energy is delivered by means of electric current alternating between electrodes spaced/separated from inner areas of the blood vessel walls, application of RF technology provides higher safety compare to other methods. Therefore, possibility of damaging adjacent walls/tissues of blood vessels is minimized.

In a manner previously discussed, detector and/or sensor 196 can be provided at the distal end of the catheter for determining physical and chemical composition of the occlusion and by means of the computer or microchip of the control unit to adjust functionality of RF emitters.

Figure 10:
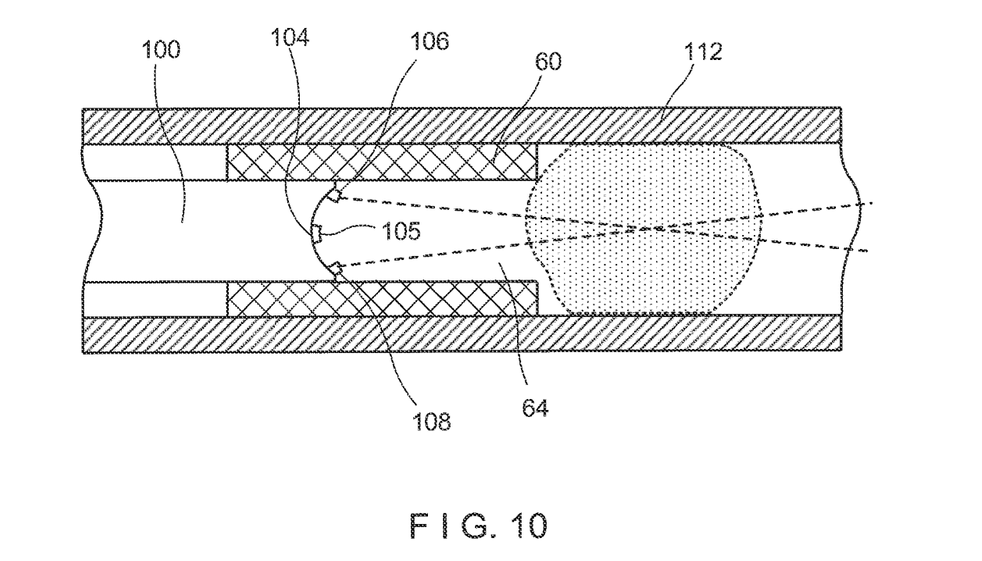
FIG. 10 is a section view of the embodiment shown in FIG. 9.

The embodiment of FIGS. 9 and 10 was discussed with the source (generator) of ultrasound energy being disposed at the proximal end of the catheter. However, use of other energy generators is also within the scope of the invention. For example, the catheter can be provided with a cavitation source disposed at the distal end to deliver cavitation waves to be used in the intrabody surgery. In use the catheter passes through/positioned within the blood vessels (veins or arteries), so that such waves destroy or affect a soft tissue or an organ in a certain desirable way through mechanically or chemical-mechanical properties and/or forces. Outlets emitting cavitation energy can be added to the distal end of an existing catheter.

According to one embodiment of the invention the cavitation energy outlets are positioned on the outer diameter of the catheter tip and disposed at the longitudinal axis passing through the catheter. This facilitates focusing the cavitation waves at the central area of the occlusion. In this arrangement while the occlusions destroyed, the risk of damage to the blood vessel walls is substantially reduced or minimized.

As previously discussed, detector and/or sensor are provided at the distal end of the catheter capable determining physical and chemical composition of the occlusion and by means of the computer or microchip of the control unit to adjust performance of the cavitation energy outlets.

Figure 16:
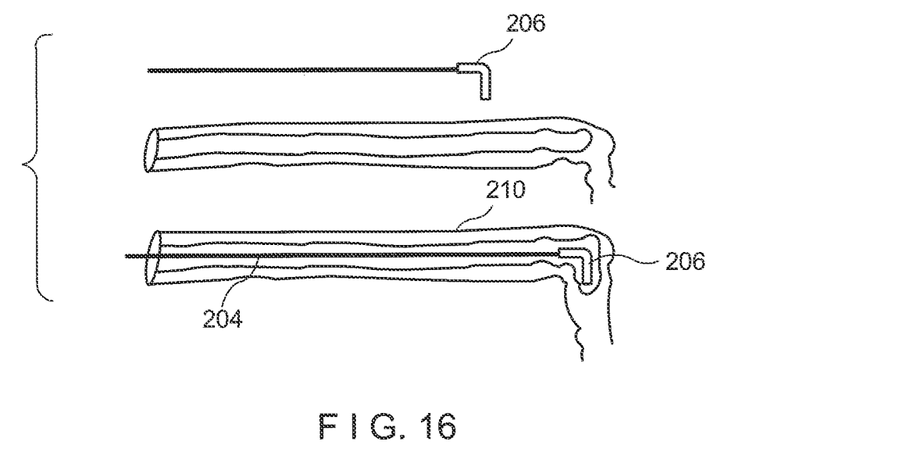
FIG. 16 illustrates one embodiment of the invention utilizing a stiffening mandrel or wire.

Turning now to FIG. 16 showing that a stiffening mandrel or wire 206 can be inserted through the bore or lumen of a hollow guidewire 204 to cause a corresponding bend in the hollow guide wire distal end. The stiffening mandrel or wire is utilized by the invention to target the distal end of the catheter in required direction within the vasculature as well as to target a desired area on the tissue by properly navigating the ablative tip. FIG. 16 illustrates a specific application of this feature of the invention, wherein 90-degree corner mandrel 206 is pushed through hollow flexible guidewire 204 to guide it through a 90 degree turn in vasculature.

Figure 17:
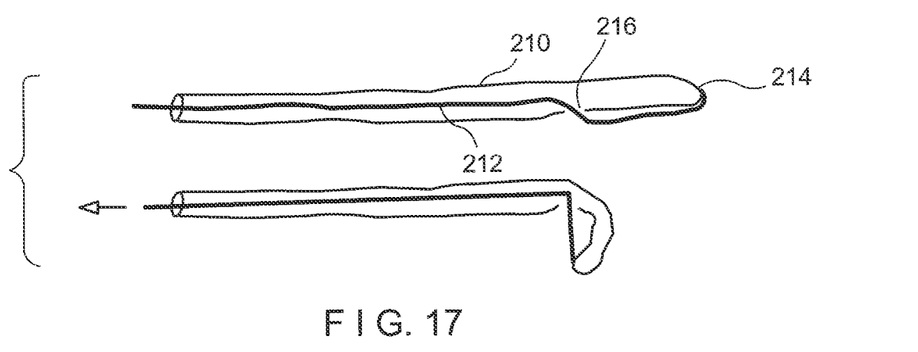
FIG. 17 illustrates an embodiment utilizing a pulling string or wire.

As illustrated on FIG. 17 a hollow guide wire 210 can also include a string 212 attached to the exterior part of the distal end 214. As further illustrated, the string 212 enters into the internal hollow part of the guidewire through a hole 216 located at predetermined optimal distance from the distal end. In this embodiment by pulling the string 212 an operator can remotely manipulate and/or bend the distal area of the guide wire 210 to an optimum angle thus targeting the distal end into required direction within the patient body lumens.

Figure 18:
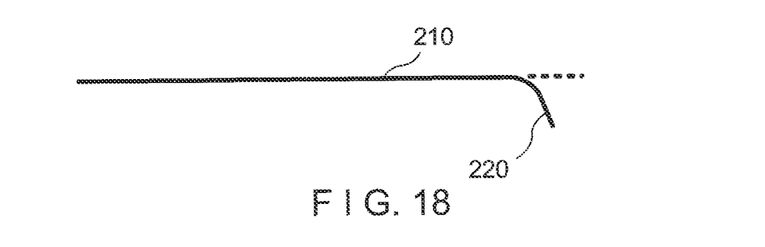
FIG. 18 illustrates another embodiment utilizing a stiffening mandrel or wire.

As illustrated on FIG. 18 a distal end 220 of a guidewire 210 can include a bend or curved portion which facilitates navigation of the guidewire in vasculature. Although various angles of inclination of the distal end to the remaining part of the guide wire are contemplated, in the preferred embodiment the distal end 210 is inclined at 30-degree angle.

What is claimed is:

1. A device for intrabody surgery, comprising:
a primary processing unit having outer and inner areas, a drive shaft passing through the inner area, a cutting element provided at a distal end of the drive shaft, the inner area is formed with a chamber with a conveying member rotationally positioned thereinside, raised surfaces extending outwardly from the conveying member within the chamber, a sleeve movable along the outer area of the primary processing unit between expanded and contracted positions, the sleeve having an outer wall with a front edge and defining an interior hollow space, at least a part of the cutting element located within the interior hollow space, a plurality of ridges extends from an inner wall of the chamber to cooperate with the raised surfaces of the conveying member; and
a primary cutting region is defined by a plurality of blades and an auxiliary cutting region is formed at the front edge of the sleeve;
wherein in use upon approaching an occlusion, the blades of the primary cutting region remove a central area of the occlusion, and the front edge of the sleeve the auxiliary cutting region removes a peripheral tissue of the occlusion at an inner wall of an intrabody lumen.

2. The device of claim 1, wherein the cutting element comprises a hub and the plurality of blades arranged at the hub, each said blade extends in a plane transverse to an axis of rotation of the cutting element.

3. The device of claim 1, wherein a plate having a plurality of holes is positioned within the chamber transversely to a longitudinal axis thereof, wherein a material cut by the cutting element is transported by the conveying member within the chamber for passage through the holes of the plate.

4. The device of claim 1, wherein the conveying member is an auger type arrangement conveying the cut material away from the operative site.

5. The device of claim 1, wherein a gap is provided between the conveying member and the ridges, to facilitate movement of the cut material within the chamber.

6. The device of claim 1, further comprising a secondary processing unit co-axially arranged with the primary processing unit, the secondary processing unit comprising a secondary chamber with a secondary conveying member.

7. The device of claim 6, wherein the secondary processing unit further comprises a secondary plate having a plurality of secondary holes, each said secondary hole having size smaller than size of the plurality of holes in the plate of the primary processing unit, wherein the cut material initially processed in the primary processing unit is transferred by the secondary conveying member for passage through the plurality of smaller size secondary holes.

8. The device of claim 1, wherein the auxiliary cutting region includes an abrasive material or a cutting element provided at the front area of an outer band.

9. A device for intrabody surgery, comprising:
a processing unit having outer and inner areas, a drive shaft passing through the inner area, a cutting element provided at a distal end of the drive shaft, the inner area is formed with a chamber with a conveying member rotationally positioned thereinside, raised surfaces extending outwardly from the conveying member within the chamber,
the cutting element is formed by a hub, a plurality of blades extending outwardly from the hub and an outer band having a front area and arranged at an outer periphery of the blades, a plurality of ridges extends from an inner wall of the chamber to cooperate with the raised surfaces of the conveying member;
a primary cutting region is defied by the plurality of blades and an auxiliary cutting region is defined by the front area of the outer band;
wherein in use upon approaching an occlusion, the blades of the primary cutting region remove or cut away a central area of the occlusion, and the outer band of the auxiliary cutting region removes a peripheral tissue of the occlusion at the inner walls of an intrabody lumen.

10. The device of claim 9, wherein the auxiliary cutting region includes an abrasive material provided at the front area of the outer band.

11. The device of claim 9, wherein the auxiliary cutting region includes a cutting element provided at the front area of the outer band.

12. The device of claim 9, wherein a plate having a plurality of holes is positioned within the chamber transversely to the longitudinal axis thereof, wherein a material cut by the cutting element is transported by the conveying member within the chamber for passage through the holes of the plate.

13. The device of claim 9, wherein the conveying member is an auger type arrangement conveying the cut material away from the operative site.

14. The device of claim 9, wherein a gap is provided between the conveying member and the ridges, to facilitate movement of the cut material within the chamber.

* * * * *